US009737384B2

(12) United States Patent
Presswood et al.

(10) Patent No.: US 9,737,384 B2
(45) Date of Patent: Aug. 22, 2017

(54) DYNAMICALLY GENERATED DENTAL ARTICULATOR CONTROLS

(71) Applicant: Robotically Generated Prosthesis, LLC, Houston, TX (US)

(72) Inventors: Ronald G. Presswood, Houston, TX (US); Ronald G. Presswood, Jr., Houston, TX (US); Jonathan Bill, Leicester (GB)

(73) Assignee: ROBOTICALLY GENERATED PROSTHESIS, LLC, Houston, TX (US)

( * ) Notice: Subject to any disclaimer, the term of this patent is extended or adjusted under 35 U.S.C. 154(b) by 0 days.

(21) Appl. No.: 14/677,613

(22) Filed: Apr. 2, 2015

(65) Prior Publication Data

US 2015/0209123 A1    Jul. 30, 2015

Related U.S. Application Data

(63) Continuation of application No. 13/641,235, filed as application No. PCT/US2011/032674 on Apr. 15, 2011, now Pat. No. 9,198,744.

(Continued)

(51) Int. Cl.
*A61C 19/00* (2006.01)
*A61C 13/34* (2006.01)
(Continued)

(52) U.S. Cl.
CPC .......... *A61C 13/34* (2013.01); *A61C 9/0006* (2013.01); *A61C 11/022* (2013.01); *A61C 11/08* (2013.01); *A61C 19/045* (2013.01); *A61C 11/06* (2013.01)

(58) Field of Classification Search
CPC ... A61C 11/002; A61C 11/022; A61C 11/025; A61C 11/027; A61C 11/06; A61C 11/08;
(Continued)

(56) References Cited

U.S. PATENT DOCUMENTS 2,768,442 A * 10/1956 De Furio ............... A61C 11/00
                                                                     433/56
3,206,852 A *  9/1965 Swanson ............. A61C 11/022
                                                                     433/56

(Continued)

FOREIGN PATENT DOCUMENTS

| CH | 666806  | 8/1988  |
| EP | 1051952 | 11/2000 |
| NL | 7706907 | 12/1978 |

OTHER PUBLICATIONS

Patent Cooperation Treaty, PCT/US2011/032674; Notification Concerning Transmittal of International Preliminary Report on Patentability and Written Opinion—Mailed Oct. 26, 2012.

(Continued)

*Primary Examiner* — Yogesh Patel
(74) *Attorney, Agent, or Firm* — Morgan, Lewis & Bockius LLP

(57) ABSTRACT

This invention relates to improved methods and apparatus for recording and simulating the condylar movement of an individual. This invention also provides a dental articulator which is designed to simulate the jaw or condylar movements of a patient. This instrument enables a dentist to obtain the necessary diagnostic information for treatment of the occlusal irregularities, such as malocclusion, and the fabrication of dental cast or "dentures".

9 Claims, 4 Drawing Sheets

Related U.S. Application Data

(60) Provisional application No. 61/325,200, filed on Apr. 16, 2010.

(51) Int. Cl.
*A61C 11/02* (2006.01)
*A61C 9/00* (2006.01)
*A61C 11/08* (2006.01)
*A61C 19/045* (2006.01)
*A61C 11/06* (2006.01)

(58) Field of Classification Search
CPC ..... A61C 11/081; A61C 11/084; A61C 11/00; A61C 11/001; A61C 11/003; A61C 11/005; A61C 11/006; A61C 13/34; A61C 9/0006; A61C 19/045
USPC ..................... 433/54–67, 213, 196
See application file for complete search history.

(56) References Cited

U.S. PATENT DOCUMENTS

| | | |
|---|---|---|
| 3,452,439 A | 7/1969 | Lee |
| 4,273,533 A | 6/1981 | Della Croce |
| 4,537,574 A | 8/1985 | Clark |
| 5,334,017 A * | 8/1994 | Lang .................... A61C 11/022 433/57 |
| 5,494,440 A * | 2/1996 | Silva .................... A61C 11/022 433/57 |
| 5,716,209 A * | 2/1998 | Faierstain ............ A61C 11/082 433/60 |
| 5,876,200 A * | 3/1999 | Tsubota ............... A61C 11/022 433/56 |
| 6,382,975 B1 * | 5/2002 | Poirier .................. A61C 1/084 433/173 |
| 7,156,657 B2 * | 1/2007 | Sasagawa ............. A61C 11/08 433/54 |
| 2003/0148244 A1 * | 8/2003 | Battistutta ............ A61C 11/00 433/65 |
| 2007/0168073 A1 | 7/2007 | Presswood et al. |
| 2010/0145898 A1 | 6/2010 | Malfliet et al. |
| 2011/0191081 A1 | 8/2011 | Malfliet et al. |
| 2011/0276159 A1 | 11/2011 | Chun et al. |
| 2012/0015321 A1 * | 1/2012 | Moriyama ......... A61C 13/0004 433/55 |

OTHER PUBLICATIONS

Patent Cooperation Treaty, PCT/US2013/025954 Notification Concerning Transmittal of International Preliminary Report on Patentability and Written Opinion—Mailed Apr. 19, 2013.

* cited by examiner

DYNAMICALLY GENERATED DENTAL ARTICULATOR CONTROLS

RELATED APPLICATIONS

This application is a continuation of U.S. application Ser. No. 13/641,235 filed Oct. 15, 2012; which is a 371 of International Application PCT/US2011/032674 filed Apr. 15, 2011; which claims benefit of provisional application No. 61/325,200, all of which are incorporated herein by reference.

TECHNICAL FIELD

The present invention relates to an improved method to make dental restorations and dentures, the tools used to make these restorations and dentures and to dental articulators and, more particularly, to an improved articulator which allows for accurate simulation of the jaw or condylar movements of a patient and accurate interchangeability of dental casts.

BACKGROUND OF THE INVENTION

Currently dentists utilize a set of impression trays to make a mold of the patient's teeth. This mold is filled will plaster to create a model of the patients teeth. The plaster model of the patient's teeth is then used by the dentist as a substructure to build either dental crowns or bridges. This model of the upper and lower dental arch is then placed in a dental articulator to allow the dentist or dental technician to make a crown or bridge. A bite transfer or some similar tool is used to align the models in the articulator. Once the upper and lower dental arch models are aligned the bite transfer is discarded. The dental technician then creates the dental restoration, crown or bridge. Once completed, the restoration is returned to the dentist for "try-in" and fitting. This fitting requires the dentist to match the restoration to the patients jaw movements.

For dentures, dentists currently utilize a set of impression trays to capture a mold of the patient's boney structure or ridge preparation for any dentures the dentist or dental technician make. This mold is filled with plaster, which is used to create a model that is then placed in a dental articulator. The dentist or dental technician will then make an educated guess as to the correct spacing between the models and as to the patients lip line. A set of "try-in" rims are created to test the assumptions made by the dentist and dental technician. The placement of the models in the articulator is then adjusted based on the modifications to the "try-in" rims. A set of "try-in" dentures is made out of wax and "tried-in" the patient's mouth. If any adjustments are made to this set of dentures, a second try-in is performed. Once these adjustments are complete, the final denture set is made from the try-in set and returned to the Dentist for final try-in and fitting.

The purpose of a dental articulator is to simulate the jaw or condylar movements of a patient. This instrument enables a dentist to obtain the necessary diagnostic information for the treatment of occlusal irregularities, such as malocclusion, and the fabrication of dental casts or "dentures."

U.S. Pat. No. 4,034,474 ("the Lee Patent") and U.S. Pat. No. 4,034,475, disclose a simplified system for measuring jaw movements, and information useful in setting and operating dental articulators. It is further suggested in those patents that plastic guide blocks of the type disclosed in the earlier Lee Patent be classified according to certain characteristics of jaw movements to provide a series of average value blocks from which the pair most closely fitting the measurements of a particular patient's condylar movements may be selected. Such guide blocks have curved walls which produce movement that closely simulates a patient's particular condylar movements, thus enabling a dentist to treat accurately an occlusal or denture problem without requiring the presence of the patient.

While these methods have been available for some time, the methods have not accurately and precisely recorded the patent's particular condylar movements. The methods currently in place fail to record the effects of both the incisal guidance and posterior guidance, in a single record, which are necessary to create a reliable non-linear duplication of the condylar guidance.

Thus there is a need for an economical and simple method to accurately replicate the unique path of motion when performing dental restorations.

BRIEF SUMMARY OF THE INVENTION

The present invention is directed to an improved method to make dental restorations and dentures. More particularly, the present invention is directed to an improved dental articulator that allows for accurate simulation of the jaw or condylar movements of a patient and accurate interchangeability of dental casts and the use of that improved dental articulator to make dental restorations and dentures.

This process is unique in at least two aspects relating to common dental practice. First, there is an expectation of recording balancing (non-working side) guides for registering the medial wall of the glenoid fossa. Second, all guidance is patient initiated and guided with verbal coaching from clinician encouraging maximal muscular effort.

In the present invention, an improved dental articulator is described. The dental articulator includes: an upper frame and a lower frame for simulating the lower dental arch and the upper dental arch; one of the frames having a pair of condyle mounted thereon; a pair of removable condylar tables mounted on the other of the frames; a malleable material deposited in the condylar tables; an incisal pin mounted to one of the frames; a removable anterior guide table; and a malleable material deposited in the anterior guide table In accordance with another aspect of this invention, a method of recording three-dimensional jaw movements and transferring the record to an improved dental articulator is provided. This method, which can be used to make dental restorations, includes the steps of: producing a standard impression of a patient's dentition; recording the functional dynamics of occlusion using impression material by having the patient perform an immediate lateral move, requesting the patient to bite back with strenuous force in right and left directions to produce a functionally generated path ("FGP") record; taking measurements using a bite plate; producing a standard model of the patient's upper dental arch and lower dental arch; placing the model of the upper arch and lower arch in the improved articulator utilizing the condylar and anterior guide setup boxes; placing the FGP record in the articulator; placing condylar and anterior guide tables in the improved articulator, the condylar and anterior guide table filled with a malleable material; manipulating the model of the upper dental arch and the lower dental arch to scribe a path into the malleable material; and removing the FGP record and allowing malleable material to harden.

In accordance with another aspect of this invention, a method of recording three-dimensional jaw movements in an edentulous patient and transferring the record to the improved dental articulator is provided. This method can be used to make dentures and includes the steps of: producing a standard impression of a patient's upper and lower jaw bone forms; placing a Vertical Dimension of Occlusion ("VDO") tool in the patient's mouth to measure the intraoral spacing between the upper and lower jaw and the lip line; attaching a spacing rim to the VDO with impression material placed on the top and bottom rear surface to the spacing rim, and placing the VDO and spacing rim in the patients mouth to record the rear spacing of the patients upper and lower jaw; placing the model of the upper arch and lower arch in the improved dental articulator utilizing the VDO and spacing rim to set the correct intraoral spacing of the upper and lower models, utilizing the condylar and anterior guide setup boxes; creating a set of Eric's rims in the improved articulator utilizing the individual patients articulation setup; Eric's rims are placed into the patients mouth to recorded the functional dynamics of occlusion by having the patient perform severally lateral moves, requesting the patient to bite back with strenuous force in right and left directions to produce a FGP record; removing the Eric's rims from the patient's mouth and using the marks indicated on the Eric's rims material is removed; returning the Eric's rims to the patient's mouth and repeating the process until the Eric's rims are fully balanced; placing the Eric's rims back into the improved articulator; placing condylar and anterior guide tables in the improved articulator, the condylar and anterior guide table filled with a malleable material; manipulating the model and Erie's rims of the upper dental arch and the lower dental arch to scribe a path into the malleable material; removing Eric's rims record and allowing malleable material to harden; and making a temporary denture of wax utilizing an improved functionally balanced Posterior Guided Occlusion teeth, that matches curve of Eric's rims and the benefits of the improved dental articulator.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying Figures. It is to be expressly understood, however, that each of the Figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying Figures and drawings, in which.

DETAILED DESCRIPTION OF THE INVENTION

As used herein, "a" or "an" means one or more than one.

The methods and apparatus of the present invention will now be illustrated with reference to FIGS. 1 through 4. It should be understood, that these are merely illustrative and not exhaustive examples of the scope of the present invention and that variations which are understood by those having ordinary skill in the art are within the scope of the present invention.

Figure 1:
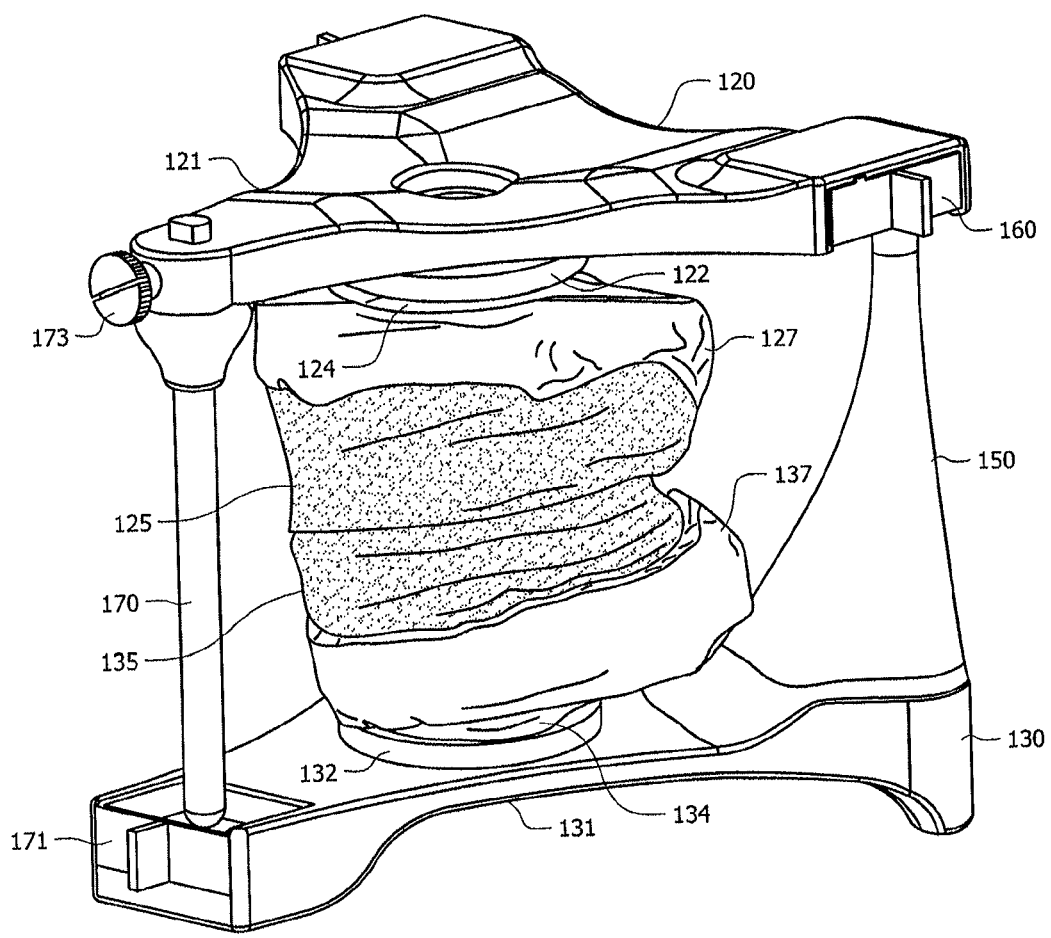
FIG. 1 shows improved dental articulator with model.
Figure 2:
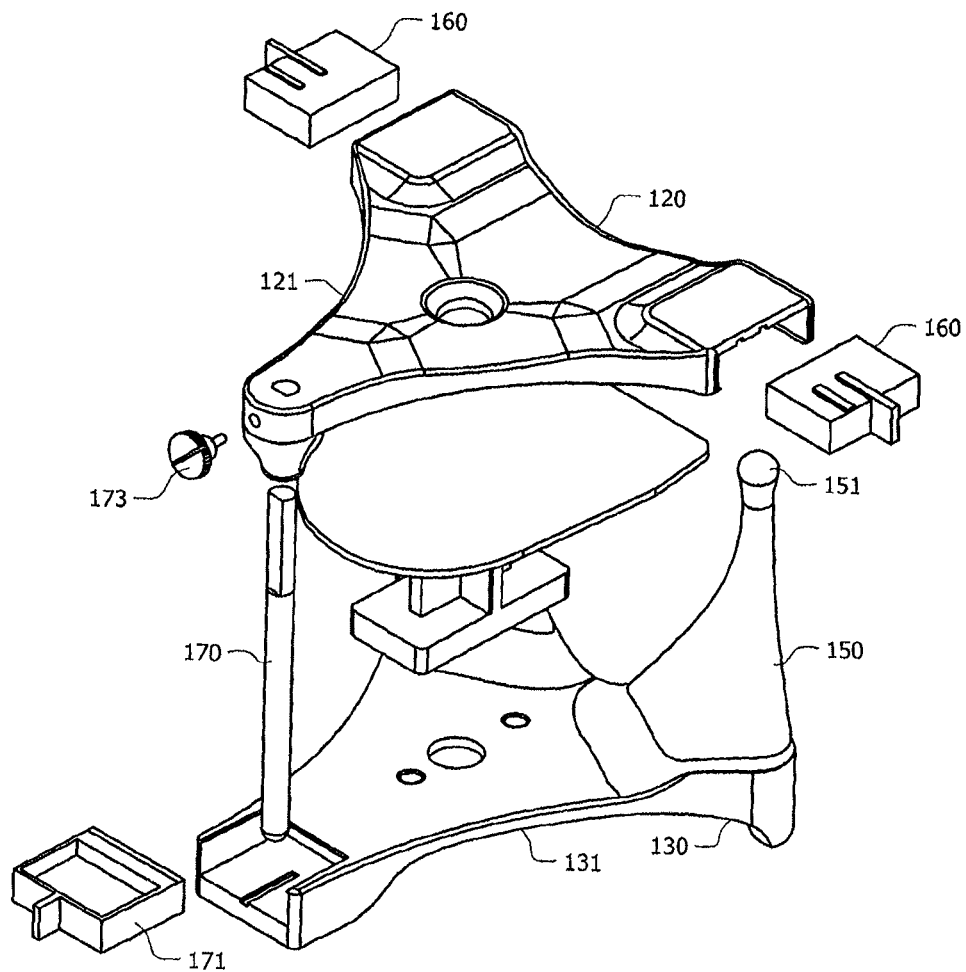
FIG. 2 shows an exploded view of the improved dental articulator.

Referring to FIGS. 1 and 2, an example of an improved dental articulator is shown. The dental articulator is used to hold models of the upper dental arch 127 and the lower dental arch 137 and simulate the movement of the jaw when fabricating dental restorations such as crowns, bridges, and dentures.

The dental articulator has an upper frame 120, and lower frame 130 used to mount the model of the upper dental arch 127 and the model of the lower dental arch 137. The model of the upper dental arch 127 is held to the arm 121 of upper frame 120 by a conventional mounting plate 122 and the model of the lower dental arch 137 is held to the arm 131 of lower frame 130 by a conventional mounting plate 132. Both models are attached to the mounting plates using plaster or other material. In the preferred embodiment, both mounting plates 132 and 142 are held to the articulator by a snapping feature or magnetic feature designed into the mounting plate; however, other securing mechanisms, such as screws and the like, are envisioned. The position of the upper dental arch 127 is adjusted by adding material to area 124 between the upper dental arch 127 and mounting plate 122. Similarly, the position of the lower dental arch 137 is adjusted by adding material to area 134 between the lower dental arch 137 and mounting plate 132.

The dental articulator has a pair of posts 150 with condyles 151. Condyle 151 fit with condylar table 160 to simulate the temporal mandible joint of the patient. The condyle can be any shape the can be used to accurately represent the motion of the of the patients jaw. However, in the preferred embodiment, a spherical shaped condyle is used.

Figure 6:
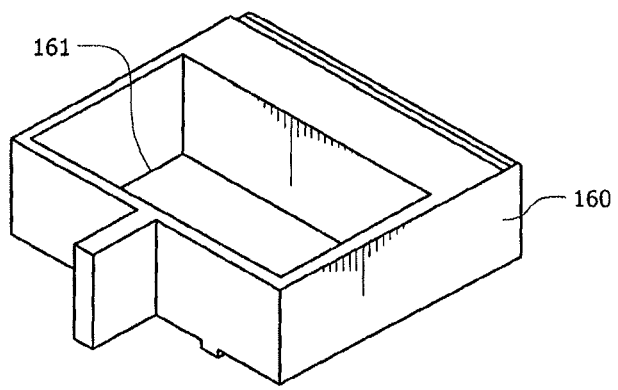
FIG. 6 shows the condylar table box.

The condylar table 160 of the present invention consists of a removable box that is connected to the dental articulator. As shown in FIG. 6, condylar table 160 includes an open box 161. The open box 161 allows a malleable material to be placed inside the box as well as to allow condyle 151 to enter the condylar table 161. The malleable material can be any self curing material such as methyl methacrylate, two part epoxy, urethane, sodium alginate, agar, condensation-cured silicones, and addition-cured silicones such as polyvinyl siloxane, wax or similar material. The setup condylar table is similar to the removable condylar table, however the box is not open, but instead includes an indentation to receive the condyle 151. The setup anterior guide table is similar to the removable anterior guide table; however the box is not open, but instead includes an indentation to receive the Incisal Pin 170. The setup condylar tables and the anterior guide table are removed and saved for future use.

Dental articulator also has an incisal pin 170 and incisal table 171. Incisal pin 170 is utilized to set the normal distance between the upper dental arch 127 and the lower dental arch 137. The incisal table 171 consists of a removable box that is connected to the dental articulator. Like the condylar table 161, the front of the box is open to allow the same malleable material as used in the condylar table 161 to be placed inside the box. This allows the incisal pin 170 to enter the incisal table 171.

Figure 5:
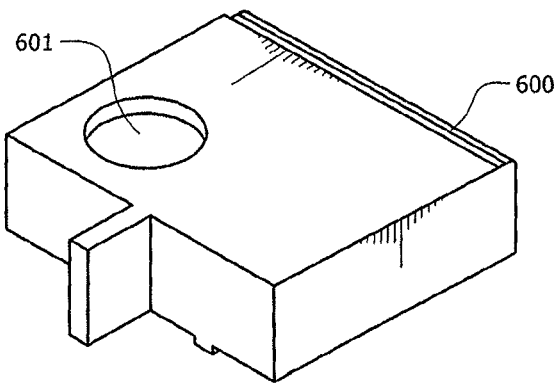
FIG. 5 shows the condylar table set-up box

Additionally, a removable set-up condylar tables and set-up incisal tables are used with the improved dental articulator. FIG. 5 shows a typical set-up table 600. The incisal pin 170 is held in place in the arm 121 by a set screw 173. The set-up table typically is a closed box or block that prevents the condyle 151 or incisal pin 170 from completely entering the box. The setup tables may also include an indentation 601 that allows the condyle 151 or incisal pin 170 to rest. This allows the dentist or dental technician to set the upper and lower arch in stable in a stable occlusal position before condylar table 160 and incisal table 170 are placed in the improved articulator.

The improved dental articulator can be used to make dental restorations and dentures. The procedure for using the improved dental articulator is described in further detail below.

Generally, the improved dental articulator can be used to make dental restorations, such as crowns and bridges, using the following steps: preparing the teeth for restoration; making an impression of the teeth; recording the jaw movements of a patient to produce a functional generated path ("FGP") record; producing the upper and lower model of the teeth; transferring the FGP record to the improved dental articulator to produce a model of the jaw movements; and reproducing the jaw movements in the articulator to create a custom condylar table. Each of these steps will be discussed in detail below.

While the following describes the method of the present invention for the restoration of a tooth, specifically the preparation of a crown, those skilled in the art will understand that this method can be applied to any dental restoration procedure and is particularly useful in restorations involving multiple teeth or restorations where a terminal tooth is missing.

Typically the first step in applying the present invention requires the preparing the tooth for the restoration. Generally the preparation of a tooth for a crown involves the irreversible removal of a significant amount of tooth structure. When preparing a tooth for a crown, typically, the enamel is totally removed and the finished preparation is, thus, entirely dentin. The amount of tooth structure required to be removed will depend on the material(s) being used to restore the tooth. For example, if porcelain is applied to a gold crown, the total tooth is reduced minimally 1.5 mm.

After the tooth is prepared, a standard impression of the dentition is made, allowing accurate models of the teeth to be made later. An impression is carried out by placing a liquid material into the mouth in a customized tray. The material then sets to become an elastic solid, and when removed from the mouth retains the shape of the teeth. Common materials used for dental impressions include, but are not limited to, sodium alginate, agar, condensation-cured silicones, and addition-cured silicones such as polyvinyl siloxane.

When crowns or bridges are made using this technique, the complex relationship that defines the functional dynamics of occlusion is recorded using a thermoplastic transfer material in a bite plate. The bite plate has a tongue and record area. The thermoplastic transfer material located in record area (re-enforced wax, compound material, or Thermacryl) is warmed to a plastic state, adapted to the prepared teeth, and the FGP registration is recorded.

Unlike the standard "chew-in" procedure, the method of this invention uses a modified procedure with more aggressive mastication used to generate the FGP record. Specifically, the patient or subject is coached into an immediate lateral move and then asked to bite back with strenuous force in right and left directions. Care is taken to ensure that the subject uses significant maximal effort when clenching the teeth together from the lateral position.

The impressions are then used to generate the models of the patient's teeth. The models of the upper and lower dental arches are mounted in an improved articulator as described above. This allows for of transferring measurements relating to the location and angle of the teeth to the articulator. Once the models of the upper and lower dental arches are mounted in the improved dental articulator, the FGP record is then placed in the articulator. The removable condylar table and the removable guide table, which are filled with a malleable material, such as a thermoplastic or other material as described above, are placed in the improved articulator. The upper and lower dental arches are then manipulated by working the upper and lower frames of the dental articulator to scribe the functional path into the malleable material stored in the condylar and anterior guide tables. Once this is complete, the FGP record is removed and the malleable material is allowed to harden.

Typically, the improved dental articulator can also be used to make dentures. The steps to make dentures using the improved dental articulator is similar to the steps used to make dental restorations, however, there are some notable differences, which are discussed further below.

While the following describes the method of the present invention for the manufacture of dentures, those skilled in the art will understand that this method can be applied to any dental restoration procedure and is particularly useful in restorations involving manufacture of full or partial dentures.

The first step in applying the present invention to make dentures requires preparing the gums for the restoration. Generally the preparation of the edentulous gums requires the creation of a special impression tray.

After the impression tray is prepared, a standard impression of the edentulous ridge is made. An impression is carried out by placing a liquid material into the mouth in the customized tray. The material then sets to become an elastic solid, and when removed from the mouth retains the shape of the gum and ridge. Common materials used for dental impressions include, but are not limited to, sodium alginate, agar, condensation-cured silicones, and addition-cured silicones such as polyvinyl siloxane.

Figure 3:
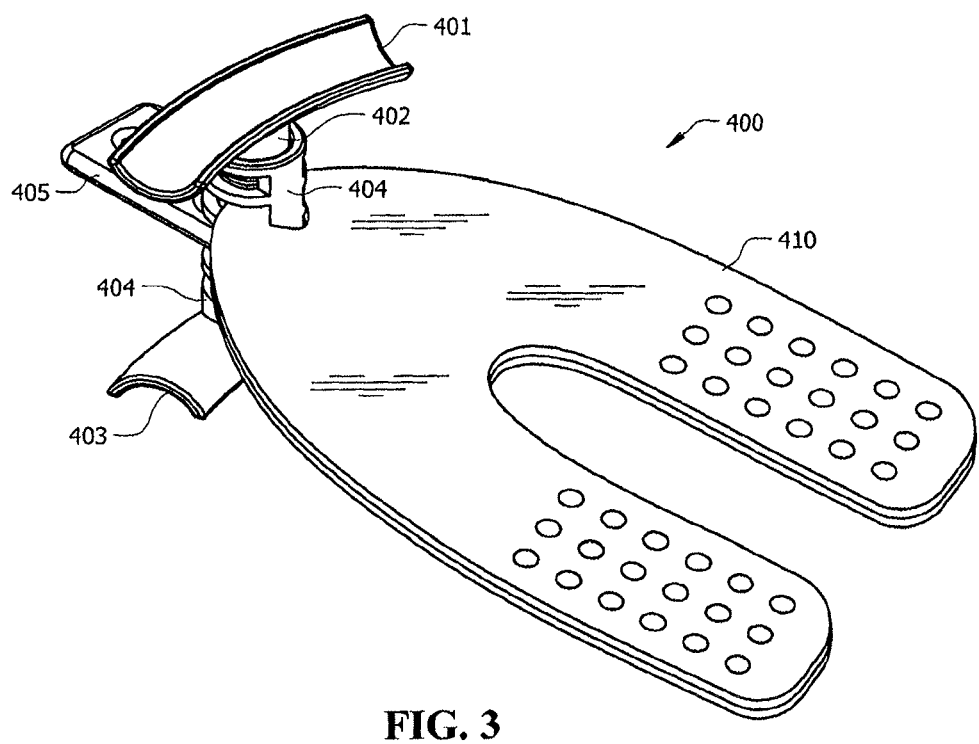
FIG. 3 shows a side view Vertical Dimension of Occlusion with Lip Line Tab.

To aid in placing the models of the patients edentulous ridge in the improved dental articulator, the intraoral spacing of the patient's mouth is measured by placing a Vertical Dimension of Occlusion ("VDO") tool in the patient's mouth to measure the intraoral spacing between the upper and lower jaw and the lip line. The VDO tool 400, which is shown in FIG. 3, has an upper rest 401, a lower rest 403, a lip line spacing tab 405 and a spacing rim 410. The upper rest 401 has a cylindrical portion 402 that slides within the cylindrical portion 404 lower rest 403 and allows the dentist to set the intraoral spacing between the upper ridge and the jaw. Once the correct intraoral spacing is adjusted, the lip line spacing tab 403 is used to mark the patients lip line and lock the adjustments in place. This is done by snapping the lip line spacing tab 403 into a notch in the cylindrical portion 404 of lower lip rest 403, which holds the cylindrical portion 402 of upper rest 401 in place. Once the intraoral spacing has been set, the spacing rim 410 is attached to the VDO tool 400 and impression material placed on the top and bottom rear surface to the spacing rim. The VDO tool 400 with spacing rim 410 are placed in the patients mouth to record the rear spacing of the patients upper and lower jaw. These measurements from VDO tool 400 are then use to place the model of the upper arch and lower arch in the improved dental articulator. Utilizing the VDO tool and spacing rim allows the correct intraoral spacing of the upper and lower models to be transferred to the model. This is typically done using the condylar and anterior guide setup boxes.

The impressions are then used to generate the models of the patient's teeth. The models of the upper and lower dental arches are mounted in the improved articulator as described above. VDO Tool 400, when used to place the dental models during the set-up of the improved articulator, allows measurements relating to the location and angle of the teeth to be transferred to the articulator.

Figure 4:
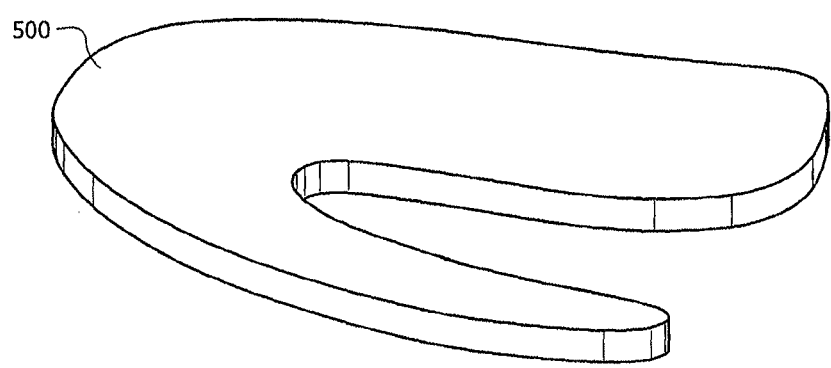
FIG. 4 shows a side view of the Eric's Rim.

Once the upper and lower models are set in the improved dental articulator, Eric's Rim bite blocks can be created in the improved articulator utilizing the individual patient's articulation setup. Eric's Rim Bite blocks, are created using a soft wax to space the Eric's rims. FIG. 4 shows a typical Eric's rim curve 500. Once created, the Eric's rims are returned to the dentist to be chewed-in by the patient.

When dentures are made using this technique, the complex relationship that defines the functional dynamics of occlusion is recorded using a thermoplastic transfer material and a unique transfer rim or Eric's Rim. The rim has a tongue and record area. The thermoplastic transfer material located in record area. This recorded area can be made from the FGP registration that is recorded in a "chew-in" procedure.

Unlike the standard "chew-in" procedure, the method of this invention uses a modified procedure with more aggressive mastication used to generate the FGP record. Specifically, the patient or subject is coached into an immediate lateral move and then asked to bite back with strenuous force in right and left directions. The Eric's rims are placed in the patient's mouth. Care is taken to ensure that the subject uses significant maximal effort when clenching the Rims together from the lateral position. Areas of contact are recorded using bite registration tape or similar material. The Rims are removed from the patient's mouth and the areas of contact are removed from the surface of the Eric's Rim using a Dental Hand Piece and a suitable burr to remove a thin layer of material where the rim's contact. This procedure is repeated until the Eric's rims are in balance. This balanced position is where there is a similar registration of contact across the rim, with no noticeable low areas or areas unmarked by the registration tape.

Once the Eric's rims are balanced, they are returned to the improved dental articulator and condylar and anterior guide tables are filled with a malleable material and placed in the improved articulator. As discussed above the malleable material can be any malleable material, the upper and lower Rims are then manipulated by working the upper and lower frames of the dental articulator to scribe the functional path into the malleable material stored in the condylar and anterior guide tables. Once the malleable material hardens the model can then be used to make a temporary denture of wax utilizing improved functionally balanced Posterior Guided Occlusion teeth that match the curve of the Eric's rims.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for making dental restorations using a dental articulator comprising an upper frame for simulating the upper dental arch and a lower frame for simulating the lower dental arch, a pair of condyles on the lower frame, one or more removable condylar tables received in the upper frame, an incisal pin on the upper frame, and a removable anterior guide table received in the lower frame, the pair of condyles configured to be moveable in the one or more removable condylar tables to allow movement of the upper frame and the lower frame with respect to each other, the incisal pin configured to interact with the removable anterior guide table, the method comprising:
    producing an impression of a patient's dentition;
    recording functional dynamics of occlusion to create a functionally generated path record;
    producing a model of the patient's upper dental arch and lower dental arch;
    placing the model of the upper arch and the lower arch in the dental articulator;
    placing the functionally generated path record in the dental articulator;
    filling the removable condylar tables and removable anterior guide table with a malleable material; and
    manipulating the model of the upper dental arch and the lower dental arch to scribe a path into the malleable material.

2. The method of claim 1 further comprising removing the functionally generated path record and allowing the malleable material to harden.

3. The method of claim 1, wherein the functionally generated path is recorded by placing impression material into the patient's mouth and having the patient bite with strenuous force in the left and right directions.

4. A method for making dentures using a dental articulator comprising an upper frame for simulating the upper dental arch and a lower frame for simulating the lower dental arch, a pair of condyles on the lower frame, one or more removable condylar tables received in the upper frame, an incisal pin on the upper frame, and a removable anterior guide table received in the lower frame, the pair of condyles configured to be moveable in the one or more removable condylar tables to allow movement of the upper frame and the lower frame with respect to each other, the incisal pin configured to interact with the removable anterior guide table, the method comprising:
    producing an impression of a patient's upper arch and lower arch;

measuring the intraoral spacing between the upper and lower jaw and the lip line;

placing the model of the upper arch and the lower arch in the dental articulator using the previously measured intraoral spacing;

creating a curved transfer rim comprising a tongue and record area, the record area comprising a transfer material;

recording, on the record area of the curved transfer rim, functional dynamics of occlusion of the patient to create a functionally generated path record;

balancing the curved transfer rim to the patient;

placing the curved transfer rim in the dental articulator;

filling the removable condylar tables and removable anterior guide table with a malleable material; and manipulating the curved transfer rim within the articulator to scribe a path into the malleable material.

5. The method of claim 4, further comprising using a condylar set-up box to set the upper arch and lower arch in a stable occlusal set-up.

6. The method of claim 4, wherein the interoral spacing between the upper and lower jaw and the lip line is measured using a vertical dimension of occlusion tool.

7. The method of claim 4, further comprising the step of removing the curved transfer rim from the dental articulator and allowing the malleable material to harden.

8. The method of claim 4, wherein balancing the curved transfer rim comprises removing transfer material deposited on the curved transfer rim until there is a similar registration of contact across the curved transfer rim based on the unique dental or jaw function of the patient, with no noticeable low areas or areas unmarked by registration tape.

9. The method of claim 4, wherein the transfer material is a thermoplastic transfer material.

* * * * *